(12) United States Patent
Crespo et al.

(10) Patent No.: US 6,248,588 B1
(45) Date of Patent: Jun. 19, 2001

(54) MEDIUM FOR PRESERVING BIOLOGICAL MATERIALS

(75) Inventors: André Crespo, Ormesson; Henri Michel Soria, Monts, both of (FR)

(73) Assignee: Aventis Pharms S.A., Antony (FR)

( * ) Notice: Subject to any disclaimer, the term of this patent is extended or adjusted under 35 U.S.C. 154(b) by 0 days.

(21) Appl. No.: 09/125,331

(22) PCT Filed: Mar. 5, 1997

(86) PCT No.: PCT/FR97/00385

§ 371 Date: Dec. 14, 1998

§ 102(e) Date: Dec. 14, 1998

(87) PCT Pub. No.: WO97/33975

PCT Pub. Date: Sep. 18, 1997

(30) Foreign Application Priority Data

Mar. 12, 1996 (FR) .................................. 96 03074

(51) Int. Cl.$^7$ .................. C12N 1/00; C12N 1/20; C12N 5/00; A01N 1/00; A01N 63/00
(52) U.S. Cl. .................. 435/404; 435/1.3; 435/2; 435/235.1; 435/325; 435/374; 424/93.1; 424/93.6; 424/93.7

(58) Field of Search .................. 485/243, 2, 1.3, 485/404, 260, 235.1, 325, 374; 424/93.1, 93.6, 93.7

(56) References Cited

FOREIGN PATENT DOCUMENTS

| 2042381 | 2/1971 | (DE) . |
| 162 332 | 11/1985 | (EP) . |
| 0 508 496 | 10/1992 | (EP) . |

OTHER PUBLICATIONS

Tomono et al., A New Intact Immunoglobulin for Intravenous Use Stabilized by Chemically Modified Gelatin Derivatives, Vox Sang. 51:81–86 (1986).

*Primary Examiner*—Deborah K. Ware
(74) *Attorney, Agent, or Firm*—F. Aaron Dubberley; Karen I. Krupen

(57) ABSTRACT

The present invention relates to a medium allowing the preservation and cryopreservation of biological materials such as animal cells and viral particles that are directly injectable or reinjectable into an organism. A medium for preserving and/or freezing biological materials, including a saline solution, modified fluid gelatin and human serum albumin, is disclosed.

47 Claims, No Drawings

MEDIUM FOR PRESERVING BIOLOGICAL MATERIALS

CROSS-REFERENCES TO RELATED APPLICATIONS

This application is a §371 national phase filing of International Application No. PCT/FR97/00385, filed Mar. 5, 1997. This application claims the benefit of foreign priority under 35 U.S.C. §119(a) of application FR96/03074, filed Mar. 12, 1996 in France.

BACKGROUND OF THE INVENTION

The present invention relates to a medium allowing the preservation and cryopreservation of biological materials such as animal cells and viral particles, which is directly injectable or reinjectable into an organism. It relates more particularly to a medium for the preservation of biological material comprising a saline solution, modified fluid gelatin and human serum albumin.

In cell therapy or gene therapy as well as in blood transfusion or bone marrow transplantation, one of the principal problems encountered is that of the preservation of biological material. It is indeed important to be able to preserve biological material, under good conditions of viability, for a sufficiently long period of time compatible with industrial scale production and storage and also to make it possible to carry out certain tests. The most commonly used method of preservation consists in freezing the said material. However, during the freezing of cells, for example, they undergo a very high stress due in particular to a phenomenon of exosmosis and to the formation of ice inside the cell. These phenomena cause numerous cell lyses both during freezing and during thawing. The capacity to divide or to differentiate of even the non-lysed cells may be irreversibly impaired. It is very important to be able to obtain a high viability level after thawing for cells which have to be injected into a living organism (blood transfusion, bone marrow transplantation or cell therapy for example), it is indeed futile to reinject dead or damaged cells. Likewise, when cells have to be recultured, it is equally important that the viability level is high. Up until now, a cryoprotectant which prevented cell lysis was added to the medium. The protecting agent most widely used and which gives the best results is a non-injectable preservative, dimethyl sulphoxide or DMSO. DMSO becomes inserted into the cell membranes and makes it possible to stabilize them. It thus prevents the destruction of the cells. A system such as this makes it possible, at the time of thawing, to have a large number of live and viable cells which are capable of dividing. However, this method poses a major problem when the said cells have to be introduced or reintroduced into an organism. Indeed, DMSO is a product which is toxic to the cells at room temperature. DMSO permeabilizes the membranes, causing the death of the cell. It should therefore be removed before being able to reimplant the cells in the case of an autograft of modified cells or to implant them in the case of a heterograft, for example, of bone marrow cells or alternatively to carry out transfusion in the case of blood cells. The elimination of the DMSO is achieved, after thawing, generally by diluting the sample in ten volumes of DMSO-free medium, followed by centrifugation and elimination of the supernatant. This operation is repeated several times until practically all the DMSO is eliminated. This treatment involves a loss of time and, by multiplying the manipulations, increases the risks of contamination by external pathogenic agents and of losses of the said biological material.

In the presence of DMSO, the percentage of viable cells after thawing is greater than seventy per cent under optimum freezing/thawing conditions as defined later. Without DMSO, this percentage is less than twenty per cent. Up until now, freezing in the presence of DMSO was the most effective and therefore the most widely used method.

BRIEF SUMMARY OF THE INVENTION

The applicant investigated a new type of medium which makes it possible to avoid manipulations subsequent to the thawing while maintaining a high percentage of viable cells. For that, the applicant developed a freezing/preservation medium which makes it possible to obtain a high viability on thawing without using DMSO or another cytotoxic cryopreservative. The advantage of such a medium stems from the fact that the solution is injectable immediately after the thawing without any manipulation being necessary. It then becomes possible to carry out the thawing directly in the operating theatre, thereby reducing the time between the thawing and use, which also makes it possible to remain constantly in a sterile medium and therefore to reduce to a minimum the risks of external contaminations.

A first subject of the invention relates to a medium for the preservation and/or freezing of biological material comprising a saline solution, modified fluid gelatin and human serum albumin (HSA).

As indicated above, this medium lacks any toxic agent and may be administered directly to an organism. It may be used for preserving, optionally in frozen form, various biological materials such as viruses, cells, platelets and the like.

DETAILED DESCRIPTION OF THE INVENTION

The first element entering into the composition of the medium according to the invention is the saline solution. The saline solution is more particularly a solution which is isotonic with the plasma. The salts entering into the composition of this solution may vary. Advantageously, it comprises chlorides, such as sodium chloride, potassium chloride, calcium chloride and/or magnesium chloride, and lactates, such as, for example, sodium lactate. More particularly, the isotonic saline solution generally comprises sodium chloride, potassium chloride, magnesium chloride and sodium lactate. According to another variant, magnesium chloride is replaced by calcium chloride. In this case, the salt concentrations of the saline solution are equivalent or practically equivalent to those of a "Ringer-lactate" solution. Such a solution is usually used in perfusion to compensate for a dehydration or a loss of physiological saline for example.

According to a specific embodiment of the invention, the saline solution is essentially composed of NaCl, $MgCl_2$, KCl and lactate whose respective final concentrations in the medium are given in Table 1 below.

TABLE 1

| Salt | Minimum concentration (g/l) | Maximum concentration (g/l) | Specific example |
|---|---|---|---|
| NaCl | 2.0 | 9 | 5.7 |
| $MgCl_2$ | 0.05 | 0.2 | 0.093 |
| KCl | 0.05 | 0.5 | 0.247 |
| Lactate | 0.5 | 4 | 2.25 |

Gelatin is the second constituent entering into the composition of the medium according to the invention. It is a protein composed of various amino acids linked by adjacent amino and carbonyl groups, so as to give the conventional peptide bond. The molecular weight of gelatin is characteristic and high (the average molecular weight values vary from about 10,000 to 100,000) and it is substantially heterogeneous for a given gelatin type or quality. Gelatin is composed of rod or asymmetric type molecules resulting from the hydrolysis of the long chains of the polypeptide residues in the white connective tissue. Experience has shown that the primary hydrolysis of collagen occurs at intervals at reactive sites of these chains to produce a non-degraded related ideal gelatin molecule. This continues to a varying degree in a secondary hydrolysis at random intervals on the less reactive bonds of the ideal gelatin molecule. This explains how the degradation reaction is responsible for the random heterogenous molecular pattern of a specific gelatin sample. Likewise, each protein constituting the gelatin has a defined isoelectric point at which the ionization and, consequently, the physical and chemical reactivity is minimal. These properties are especially the solubility, the viscosity and the colloidal osmotic pressure. The asymmetry of the gelatin molecule therefore gives, with the heterogenous molecular pattern, intrinsic properties of gel formation and viscosity to the gelatin solutions prepared for the medium according to the invention.

The gelatin itself (sterilized and freed from pyrogenic and antigenic substances) has already been used as product for replacing blood plasma, but it has raised a number of problems, in particular for its preservation, because it gels at room temperature. This has led to other compounds derived from gelatin, generally designated by the term modified fluid gelatin, which make it possible to overcome these disadvantages in particular.

Among the modified fluid gelatins, there may be mentioned for example oxypolygelatin, obtained by polymerization of gelatin with glyoxal and oxidation with $H_2O_2$. Other modified fluid gelatins are obtained by reacting gelatin (preferably having a molecular weight range of about 15,000 to 36,000) with succinic, citraconic, itaconic, aconitic or maleic anhydride or succinyl or fumaryl chloride, as described in French patent No. 1,291,502. All these gelatin derivatives are compatible with a pharmaceutical use and may be introduced into the blood stream directly in an isotonic saline solution. Modified fluid gelatins have also been described in patents U.S. Pat. Nos. 2,525,753, 2,827, 419 and 3,108,995.

More generally, the modified fluid gelatins according to the invention consist of chemically modified collagen hydrolysis products which are compatible with a pharmaceutical use. They are preferably products having an average molecular weight of between 10 kD and 100 kD, and still more preferably between 15 kD and 40 kD. They are preferably modified by reacting with an anhydride, so as to obtain a final product, having a fluidity adapted to the desired use, according to the teachings, for example, of patent FR 1,291,502. This is preferably succinic, citraconic, itaconic, aconitic or maleic anhydride. A particularly advantageous modified fluid gelatin consists of the hydrolysis product of collagen having an average molecular weight of between 15 kD and 40 kD, modified by reacting with succinic anhydride. The modified fluid gelatins according to the invention may be prepared by the techniques of persons skilled in the art, which are especially described in the abovementioned patents.

The third element entering into the composition of the medium according to the invention is human serum albumin. Human serum albumin (HSA) is a non-glycosylated monomeric protein of 585 amino acids, with a molecular weight of 66 kD. Its globular structure is maintained by 17 disulphide bridges which create a sequential series of 9 double loops (Brown J. R., "Albumin Structure, Function and Uses", Rosenoer, V. M. et al. (eds.) Pergamon Press, Oxford (1977) 27–51). The genes encoding HSA are known to be highly polymorphic, and more than 30 apparently different genetic variants have been identified by electrophoretic analysis under varied conditions (Weitkamp, L. R. et al., Ann. Hum. Genet. 37 (1973) 219–226). The HSA gene is cut in 15 exons by 14 intron sequences and comprises 16,961 nucleotides, from the supposed "capping" site up to the first site of addition of poly(A).

Human albumin is synthesized in the hepatocytes of the liver, and then secreted into the blood flow. This synthesis leads, in a first instance, to a precursor, prepro-HSA, which contains a signal sequence of 18 amino acids directing the nascent polypeptide in the secretory pathway.

HSA is the most abundant blood protein, with a concentration of about 40 g per litre of serum. There are therefore about 160 g of circulating albumin in the human body at any time. The most important role of HSA is to maintain a normal osmolarity of the blood flow. It also has an exceptional binding capacity for various substances and plays a role both in the endogenous transport of hydrophobic molecules (such as steroids and bile salts) and in that of different therapeutic substances which may thus be transported to their respective sites of action. Furthermore HSA has been recently implicated in the breakdown of the prostaglandins.

The HSA used within the framework of the present invention may be either of natural origin (purified HSA) or of recombinant origin (rHSA).

In this regard, the natural HSA is generally produced by purification from biological material of human origin. In particular, it is obtained by conventional techniques for fractionation of plasma obtained from blood donations (Cohn et al., J. Am. Chem. Soc. 68 (1946) 459 pp), or by extraction from the human placenta, according to the technique described by J. Liautaud et al. (13th International IABS Conference, Budapest; A: "Purification of proteins. Development of biological standard", Karger (ed.), Bale, 27 (1973) 107 pp). Preferably, the purified albumin used within the framework of the present invention is a plasma albumin. Most particularly, a commercial plasma albumin solution may be used.

The development of genetic engineering and of new extraction and purification techniques has opened the possibility of obtaining, at a lower cost price, improved products of higher purity, of greater stability and without risk of viral contamination (for example hepatitis B and AIDS). Given the importance of the HSA market, the possibility of producing this protein by a recombinant route has been widely studied. Thus, numerous expression systems have been studied for the preparation of the recombinant HSA.

More particularly, as regards the bacterial hosts, the first genetic engineering experiments used the bacterium *E. coli* as host organism. Thus, European patents EP 236 210, EP 200 590, EP 198 745, or EP 1 929 describe processes for the production of HSA in *E. coli* using different expression vectors, different transcriptional promoters, and different secretory signals. Subsequently, studies relating to the secretion of HSA in *Bacillus subtilis* were also carried out (Saunders et al., J. Bacteriol. 169 (1987) 2917). As regards the eukaryotic hosts, processes for the production of HSA were developed using yeasts as host organism. Thus, it has been possible to demonstrate the production of HSA under the control of the chelatin promoter in *S. cerevisiae* (Etcheverry et al., Bio/Technology 4 (1986) 726). The production of HSA has also been mentioned in the brewery yeast during the manufacture of beer, using a post-fermentative process (EP 201 239). More recently, patent application EP 361 991 describes a particularly efficient system using the yeast Kluyveromyces as host organism, transformed with vectors derived from the plasmid pKD1. Particularly high levels of HSA secreted into the culture medium were able to be obtained with this system. Finally, the production of recombinant HSA has also been described in Pichia pastoris, (EP 344 459). In addition, the purification of HSA has also been the subject of numerous studies (EP 319 067).

A recombinant or natural HSA is advantageously used which meets certain quality criteria (homogenetic, purity, stability). Thus, the pharmacopoeia sets a number of parameters for the plasma albumin solutions, namely a pH value, a protein content, a polymer and aggregate content, an alkaline phosphatase content and a certain protein composition. It imposes, furthermore, a certain absorbance, the compliance with a test of sterility, with a test of pyrogens and of toxicity (see "Albumini humani solutio" European Pharmacopoeia (1984) 255). The use of an albumin corresponding to these criteria, although not essential, is particularly preferred.

Advantageously, the compositions according to the invention comprise a purified human plasma albumin or a recombinant human albumin, preferably produced in an eukaryotic host. In addition, the term HSA comprises, for the purposes of the invention, any natural variant of human albumin, resulting from the polymorphism of this protein. It is also possible to use an HSA equivalent, that is to say any HSA derivative conserving the properties of HSA. These derivatives may be especially N-terminal fragments of HSA.

The media according to the invention may be prepared in various ways. The different components may be mixed together, and then the biological material added to the mixture. It is also possible to mix one or two components with the biological material and then to add the last or the last two component(s). Preferably, a medium comprising the three components is prepared, to which the biological material is then added. The preparation of the medium and the addition of biological material are performed under sterile conditions. According to a specific embodiment, the modified fluid gelatin is added to a saline solution, and then the HSA is added to the medium. In this regard, a preferred embodiment consists in using a specific mixture having the same composition as a blood plasma substitute, Plasmion (patent FR 2,042,381), to which the HSA is then added. Plasmion is a commercial solution composed of a saline solution and modified fluid gelatin. Its composition is the following:

| | |
|---|---|
| Modified fluid gelatin | 30 g/l |
| Sodium chloride | 5.382 g/l |
| Magnesium chloride | 0.143 g/l |
| Potassium chloride | 0.373 g/l |
| Sodium lactate | 3.360 g/l |
| Water for injection qs 1000 ml | |

Plasmion is usually used as vascular filling solution in the restoration of the circulating blood volume, or for a haemodilution with a reduction in blood viscosity and an increase in the microcirculation, or alternatively for the restoration of the ionic equilibrium and the prevention of acidosis. A preferred subject of the present invention relates to a medium allowing the preservation and/or freezing of biological material in which plasmion serves as mixture of saline solution and modified fluid gelatin. Such a medium comprises plasmion and human serum albumin.

The respective proportions of the components of the media according to the invention may be adapted by persons skilled in the art according to the biological material considered. As illustrated in the examples, although certain concentration ranges are preferred, the proportions may be modified. In this regard, the preferred salt concentration intervals were presented in Table 1 above. As regards the gelatin and the serum albumin, they vary preferably in an albumin/gelatin weight ratio of between 0.5 and 100. This ratio is more preferably between 0.5 and 60, and in a particularly preferred manner, between 3 and 15. By way of specific examples, there may be mentioned ratios of 0.74, 1.66, 3.3, 6.66, 13.4, 26.66 and 60. These various ratios correspond to media according to the invention containing from 10% to 90% by volume of a commercial plasmion solution and from 90% to 10% by volume of a human serum albumin solution at 20%. Different compositions are represented by way of illustration in Table 2 below.

TABLE 2

| Plasmion % v | Gelatin Weight (g/l) | HSA 20% % v | HSA Weight (g/l) | Empirical ratio HSA/gelatin |
|---|---|---|---|---|
| 10 | 3 | 90 | 180 | 60 |
| 90 | 27 | 10 | 20 | 0.74 |
| 80 | 24 | 20 | 40 | 1.66 |
| 20 | 6 | 80 | 160 | 26.66 |
| 50 | 15 | 50 | 100 | 6.66 |
| 67 | 20 | 33 | 66 | 3.3 |
| 33 | 10 | 67 | 134 | 13.4 |

In general, the medium according to the invention contains from 10 to 90% by volume of plasmion respectively of human serum albumin solution at 20%. The specific embodiments are media comprising between 20 and 80% of plasmion respectively of human serum albumin solution at 20%, more preferably between 33 and 67% of plasmion respectively of human serum albumin solution at 20%. Another specific embodiment of the invention consists in a mixture of plasmion and human serum albumin solution at 20% in a volume to volume ratio of 50/50. Advantageously, the HSA/gelatin weight ratio is between 2 and 7. Particularly remarkable results have been obtained with a ratio of about 3.

Moreover, additional components may be added to the media according to the invention. In particular, biocompatible cell stabilizing agents may be introduced, such as for example compounds of the glycerol family (glycine, glycerol, sucrose, glucose, and the like). These compounds are present in the media of the invention in quantities of less than 5% by weight. Preferably, the media according to the invention comprise between 0.5 and 5% by weight of glycine or glycerol.

The media according to the invention serve for the storage, preservation and freezing of biological material. Biological material is generally understood to mean any material containing a genetic information, which is self-reproducible or reproducible in a biological system. The said biological material may consist more particularly of cells or viral particles or both. Among the cells which may be frozen, there may be mentioned, for example, blood cells, bone marrow cells, cells producing viral particles ("packaging" lines), or genetically modified cells.

The viral particles more particularly relevant to the present invention are those which may be used in gene therapy. A large number of viruses may have their genome modified, on the one hand so that they lose their ability to multiply while retaining their infectivity, on the other hand so as to insert into their genome a nucleic acid sequence of therapeutic interest which will be expressed in the infected cells. Among these viruses, there may be mentioned more particularly the adenoviruses, the AAVs, the retroviruses, the herpes viruses and the like.

The adenoviruses are among the most widely used viruses. Different adenovirus serotypes, whose structure and properties vary somewhat, have been characterized. Among these serotypes, the use of type 2 or 5 human adenoviruses (Ad 2 or Ad 5) or adenoviruses of animal origin (see application WO 94/26914) is preferred in the context of gene therapy. Among the adenoviruses of animal origin which can be used, there may be mentioned the adenoviruses of canine, bovine, murine, (example: MAV1, Beard et al., Virology 75 (1990) 81), ovine, porcine, avian or simian (example:SAV) origin. Preferably, the adenovirus of animal origin is a canine adenovirus, more preferably a CAV2 adenovirus [manhattan strain or A26/61 (ATCC VR-800) for example]. Preferably adenoviruses of human or canine or mixed origin are used.

The defective adenoviruses comprise the ITRs, a sequence allowing encapsidation and a nucleic acid of interest. In the genome of these adenoviruses, at least the E1 region is non-functional. The viral gene considered may be made non-functional by any technique known to persons skilled in the art, and especially by total suppression, substitution, partial deletion or addition of one or more bases in the gene(s) considered. Such modifications may be obtained in vitro (on isolated DNA) or in situ, for example, by means of genetic engineering techniques, or alternatively by treatment by means of mutagenic agents. Other regions may also be modified, and especially the region E3 (WO95/02697), E2 (WO94/28938), E4 (WO94/28152, WO94/12649, WO95/02697) and L5 (WO95/02697). It may also comprise a deletion in the E1 region at the level of which the E4 region and the nucleic acid of therapeutic interest are inserted (cf FR 94 13355).

The defective recombinant adenoviruses may be prepared by any technique known to persons skilled in the art (Levrero et al., Gene 101 (1991) 195, EP 185 573; Graham, EMBO J. 3 (1984) 2917). In particular, they may be prepared by homologous recombination between an adenovirus and a plasmid carrying, inter alia, the DNA sequence of interest. The homologous recombination occurs after co-transfection of the said adenoviruses and plasmid into an appropriate cell line. The cell line used should preferably (i) be transformable by the said elements, and (ii), comprise the sequences capable of complementing the defective adenovirus genome part, preferably in integrated form in order to avoid the risks of recombination.

Next, the adenoviruses which have multiplied are recovered and purified according to conventional molecular biology techniques, generally on a caesium chloride gradient.

As regards the adeno-associated viruses (AAV), they are DNA viruses of a relatively small size, which integrate into the genome of the cells which they infect, in a stable and site-specific manner. They are capable of infecting a broad spectrum of cells, without inducing any effect on cell growth, morphology, or differentiation. Moreover, they do not appear to be involved in pathologies in man. The AAV genome has been cloned, sequenced and characterized. It comprises about 4,700 bases, and contains, at each end, an inverted repeat region (ITR) of about 145 bases, serving as replication origin for the virus. The rest of the genome is divided into 2 essential regions carrying the encapsidation functions: the left part of the genome, which contains the rep gene involved in the viral replication and the expression of the viral genes; the right part of the genome, which contains the cap gene encoding the virus capsid proteins.

The use of AAV-derived vectors for the transfer of genes in vitro and in vivo has been described in the literature (see especially WO 5 91/18088; WO 93/09239; U.S. Pat. Nos. 4,797,368, 5,139,941, EP 488 528). These applications describe different AVV-derived constructions, in which the rep and/or cap genes are deleted and replaced by a gene of interest, and their use to transfer in vitro (on cells in culture) or in vivo (directly in an organism) the said gene of interest. The defective recombinant AAVs may be prepared by co-transfection, into a cell line infected by a human helper virus (for example an adenovirus), of a plasmid containing a nucleic acid sequence of interest bordered by two AAV inverted repeat regions (ITR), and of a plasmid carrying the AAV encapsidation genes (rep and cap genes). A useable cell line is for example the line 293. The recombinant AAVs produced are then purified by conventional techniques.

As regards the herpes viruses and the retroviruses, the construction of recombinant vectors has been widely described in the literature; see especially Breakfield et al., New Biologist 3 (1991) 203; EP 453242, EP 178220, Bernstein et al. Genet. Eng. 7 (1985) 235; McCormick, BioTechnology 3 (1985) 689, and the like. In particular, the retroviruses are integrative viruses, selectively infecting dividing cells. They therefore constitute vectors of interest for cancer applications. The genome of the retroviruses comprises essentially two LTRs, an encapsidation sequence and three coding regions (gag, pol and env). In the recombinant vectors derived from the retroviruses, the gag, pol and env genes are generally deleted, completely or in part, and replaced by a heterologous nucleic acid sequence of interest. These vectors may be prepared from different types of retroviruses such as especially MoMuLV ("murine moloney leukaemia virus"; also called MoMLV), MSV ("murine moloney sarcoma virus"), HaSV ("Harvey sarcoma virus"); SNV ("spleen necrosis virus"); RSV ("Rous sarcoma virus") or Friend's virus.

To construct defective recombinant retroviruses comprising a nucleic acid of therapeutic interest, a plasmid comprising especially the LTRs, the encapsidation sequence and the said nucleic acid is constructed, and then used to transfect a so-called encapsidation cell line, capable of providing in trans the retroviral functions deficient in the plasmid. Generally, the encapsidation lines are therefore capable of expressing the gag, pol and env genes (cf below).

The generally recombinant viral particles (containing a nucleic acid of interest) and the defective viral particles (incapable of autonomous replication) may be preserved in a medium according to the invention. Generally, the viral particles (adeno, AAV, retro and the like) are used in purified form and then packaged in a medium according to the invention for their preservation, preferably in frozen form. Generally, $10^4$ to $10^{14}$ viral particles may be packaged in 1 ml of medium according to the invention, in a sterile container. Preferably, $10^5$ to $10^{10}$ viral particles are used per ml of medium and, still more preferably, $10^8$ or $10^9$.

The cell lines termed encapsidation (or packaging) lines which were earlier referred to above are cell lines used for the production of defective recombinant viruses, in vitro or in vivo (after implantation). There may be mentioned, by way of example of a line for the production of adenoviruses, the human embryonic kidney line 293 (Graham et al., J. Gen. Virol. 36 (1977) 59) which contains especially, integrated into its genome, the left part of the genome of an Ad5 adenovirus (12%) or lines capable of complementing the E1 and E4 functions as described especially in applications Nos. WO 94/26914 and WO 95/02697. There may also be mentioned encapsidation lines which have been described for the production of retroviruses or herpes viruses, and especially the line PA317 (U.S. Pat. No. 4,861,719); the line PsiCRIP (WO 90/02806) and the line GP+envAm-12 (WO 89/07150) or recombinant retrovirus-producing derived lines such as the line M11 (WO 94/13824). As illustrated in the examples, the medium of the invention is particularly adapted to the preservation of viral particle-producing cells.

Another type of biological material which may be advantageously preserved in a medium according to the invention consists of genetically modified cells. The genetically modified cells are cells, intended especially for gene therapy, into which a nucleic acid sequence of interest has been introduced. Over the past few years, the number of these cells has continued to grow and there may be mentioned, by way of examples, the haematopoietic stem cells (WO 88/08450, WO 93/20195, WO 93/09815, WO 93/11230), the endothelial cells (WO 89/05345, WO 90/06757, WO 92/09222), the myoblasts (WO 93/03768, WO 93/24151, WO 94/01129), the fibroblasts (U.S. Pat. No. 5,219,740, WO 89/02468, WO 93/07906), the hepatocytes (WO 89/07136, WO 92/12242, WO 93/03142), the astrocytes (WO 94/01135), the neuroblasts (WO 94/10292, WO 94/16059), the keratinocytes (WO 94/11011), the macrophages (FR 93/10222). These cells generally possess the capacity to produce a therapeutic product of interest and may be implanted in vivo. Among the blood cells, there may be mentioned the erythrocytes, the neutrophilic, basophilic and eosinophilic granulocytes, the B and T lymphocytes, especially the CD4 lymphocytes, the cytotoxic lymphocytes (CD8 CTL), the tumour infiltrating lymphocytes (TIL) and the LAKs, the monocytes and macrophages, the dendritic cells, the megakaryocytes and the platelets. These cells may also be genetically modified in order to acquire new therapeutic properties.

The medium according to the invention may, in addition, be used for the preservation of primary cell cultures, and of tumour cells or biopsies of tumours. This type of material is currently under study in clinical trials of immuniadoptive therapy in which a tumour is removed from a patient, treated with different immunopotentiating agents (introduction of genetic material expressing lymphokines or tumour antigens) and then readministered to the patient. One of the difficult steps lies in the preservation of the cells removed from the patient or modified before reinfusion. The medium of the invention advantageously allows a good preservation of these materials with a high viability.

The use of a medium according to the invention makes it possible to preserve these cells and to inject them directly into an organism, without a centrifugation or washing stage, with a good viability and without affecting their capacity to produce therapeutic proteins or viruses, where appropriate.

To this end, the present invention also relates to preparations containing the preservation medium according to the invention and biological material, as well as to a process for the storage of biological material. The said biological material may be packaged directly in a medium according to the invention. As regards cells, these are advantageously previously freed of their culture medium (for example centrifuged, harvested and washed in a buffer solution), before being packaged in a medium according to the invention. As regards proliferative cells, they are preferably used at sub-confluence, at the exponential growth phase. As indicated in the examples, it is under these conditions that the best viability results may be obtained. It is possible, however, to use cells at confluence or post-confluence. Generally, $10^5$–$10^9$ cells are packaged per ml of medium and, more preferably, $10^6$–$10^8$. In the case of adherent cells, the cells are previously detached by conventional treatment, suspended and then packaged in a medium of the invention. The treatment used to detach the cells may be an enzymatic treatment (trypsin for example), a chemical treatment (detergent) or a mechanical treatment. In the case of a chemical or enzymatic treatment, the cells are then centrifuged and washed in order to remove the enzyme or the detergent, before freezing. Generally, the viability of the cells is controlled before freezing, as well as their sterility. As regards viruses, these are previously purified as indicated above (centrifugation on a caesium chloride gradient for example, chromatographies and the like). They may be packaged at the rate of $10^4$ to $10^{14}$ particles per ml, preferably $10^5$ to $10^{10}$. The biological material may then be packaged in the medium according to the invention, in an appropriate container. It may be an ampoule, a tube, especially a cryotube, a bag, a vial, a flask and the like. The container is previously sterilized and the packaging operations are performed under sterile conditions.

A medium according to the invention allows the freezing and thawing of biological material under conditions of high viability. The media according to the invention may, in particular, allow the freezing of biological material at temperatures of between −200 and −4 degrees Celsius. The material may be preserved especially in liquid nitrogen or at higher temperatures, for a period which is sufficiently long to ensure the preservation of an industrial stock (up to one year for example). The percentage of viable cells after thawing is defined as the number of live cells divided by the total number of cells multiplied by one hundred. This percentage viability in a medium according to the invention is advantageously greater than 50%. Preferably, this percentage is greater than 60%. Most preferably, this percentage is greater than 70%.

Other advantages of the present invention will appear on reading the following examples which should be considered as illustrative and non-limiting.

Materials and Methods

Test of Cell Viability

The viability of the cells was determined by the trypan blue technique. Trypan blue is a dye which penetrates only into dead cells. When the very regular grid of a Malassez cell or of a Kova slide is observed, the cells which are in the small squares of the grid as a whole are contained in a very precise volume: 1 μl. These are the cells which are counted, while observing the following rules:

The cells which are on the outer limits of the grid are counted only if they are on the upper and left edges (green) or on the lower and right edges (red);

For the counting to be significant, count two counting chambers and calculate the mean.

The number of dead cells corresponds to the number of blue cells. The number of viable cells corresponds to the number of refringent white cells. The viability is expressed by the ratio of the number of viable cells to the number of viable cells plus the number of dead cells.

It is understood that other techniques for counting or determining cell viability may be used.

Cells Used

The cells used in the examples are genetically modified fibroblasts capable of producing viral particles. They are more precisely of the cell line M11 deposited at the Collection Nationale de Culture de Microorganismes, under the reference I-1278. This line derives from the PsiCRIP cells.

Equivalent cells are for example the cells of the Am12 line (WO 89/07150). It is understood that the process described is directly applicable to other cells, especially of human origin, whether they are primary cultures or established lines.

Albumin

The albumin used in the context of the examples is marketed by the company Armour under the reference Albumin A or human plasma Albumin 20%. It is understood that any other source of albumin may be used.

Plasmion

Plasmion is of commercial origin (Roger Bellon, France).

EXAMPLES

Example 1

Procedure for Freezing the Biological Material

For the freezing of cells, it is preferable to use subconfluent cells at the exponential growth phase. Moreover, to improve the monitoring of the biological material, the distribution and freezing, in cryotubes, of the cell suspension after bringing into contact with the freezing medium according to the invention are carried out as rapidly as possible. Finally, the manipulations are performed under sterile conditions (for example in a laminar flow cabinet).

This example describes more particularly a procedure for freezing cells (genetically modified cells, blood cells, virus producing cells and the like). It is understood that this procedure may be adapted by persons skilled in the art to the freezing of virus or other material.

The culture flasks containing the cells to be frozen are taken out of the incubator, and placed under a microscope, so as to check the appearance of the culture. If one or more flasks have a non-conforming appearance (detached cells, confluent cells, cloudy culture, non-refringent cells, impaired flask, and the like), it is not used for the freezing.

The conforming flasks are then transferred into a laminar flow cabinet. When the cells are adhering cells, they are treated so as to detach them and/or dissolve the aggregates. For that, it is possible to use trypsin or any other dissociating medium (detergent, and the like). The cell suspensions are then combined in a sterile flask and gently homogenized by pipetting. An aliquot of 1 ml is removed for the counting. If the viability of the culture is less than 80%, the cell suspension is rejected.

The suspension is then distributed, equally (for example using a pipette) into an even number of centrifugation tubes and then centrifuged for 10 minutes at 400 g.

The containers for freezing using alcohol are transferred to the cabinet, as well as a flask of freezing medium at +4° C. The volume of freezing medium necessary to obtain a cell concentration of $10^7$ viable cells per ml is then placed in a sterile flask.

After centrifugation, the supernatant is removed and then the pellets are taken up in aliquots of cold freezing medium. The suspensions are homogenized and taken up in the flask containing the freezing medium, and again homogenized. A sample is collected for the test of sterility.

The cell suspension is then distributed in the cryotubes, which are then placed immediately in the container for freezing using alcohol. The containers are transferred for 1 hour at +4° C. and then placed in a chamber at −80° C. for at least 12 h, preferably 24 h. At least 24 h after freezing, the ampoules are removed from containers with alcohol and stored in a container with liquid nitrogen.

Example 2

Procedure for Thawing the Biological Material

A. Products used

Trypan blue

Sterile phosphate buffer (PBS), pH 7.2

Ethanol 70%

Culture medium

Foetal calf serum (FCS)

Sterile pot of water at 37°±0.5° C. (50 to 200 ml)

B. Procedure

The freezing is advantageously performed under sterile conditions, for example in a safety cabinet.

In a 50 ml sterile tube, prepare a volume of culture medium at 20% FCS corresponding to 9/10 of the volume of the batch (of the ampoule) to be thawed (thawing medium). Thus, 7 ml of culture medium plus 2 ml of FCS are prepared in the case of a 1 ml ampoule.

The ampoule to be thawed is dipped into the pot of sterile water at about 37 degrees Celsius, without submerging it, with gentle stirring until the ice completely disappears. Rapidly wipe the ampoule with 70% ethanol. Pipette the contents of the ampoule and transfer it into the tube containing the thawing medium and then, without changing the pipette, reaspirate an identical volume and rinse the ampoule once. Gently homogenize the suspension and collect 1 ml in a sterile tube for counting. Depending on the counting result, the cell suspension is transferred into a culture flask, diluting with the quantity of thawing medium necessary to obtain an initial cell concentration of between 2.0 and $3.0\times10^5$ viable cells per millilitre of culture.

To allow the cell viability after thawing to be monitored over time, the culture flask is then placed in the $CO_2$ incubator at 37° C.±0.5; or in the case of HEPES buffered medium, in a hot chamber at 37° C.+0.5.

In the case of therapeutic applications, only one aliquot of the contents of the ampoule is used for the test of cell viability and sterility. If there is conformity, the contents of the thawed ampoule may then be directly injected.

Example 3

Study of the Percentage Viability After Freezing and Thawing of Retrovirus-producing Cells in Different Media According to the Invention.

The cells used in this example are recombinant retrovirus producing cells of the M11 line. The cells are used at the exponential growth phase. The cells were frozen according to the general procedure described in Example 1. For this, the cells were detached from the dish with the dissociating medium (1×PBS: 0.02% EDTA): 3 ml per T75 dish; 5 ml per T160 or T225 dish. The cells are incubated for 5 min in this medium, with gentle stirring, and then recovered in a Falcon tube. An aliquot is used to count the cells. The suspension is then centrifuged for 5 min at 1000 rpm at 20° C. The cells are then distributed into freezing ampoules containing 1 ml of medium according to the invention, at the rate of $10^7$ cells per ml. The different media tested are described below (Table 3). The ampoules are frozen according to the procedure described in Example 1. At a determined date, the ampoules are thawed according to the procedure described in Example 2, and the cell suspension is transferred into culture flasks 37° C., 5% $CO_2$. The cell viability is determined as indicated in Materials and Methods. The results obtained are presented in the following tables 4–10. They clearly show a high percentage viability in the presence of a medium of the invention. Thus, more than 70% of cells are viable for certain media of the invention. In general, the cell viability is always greater than 50%. It should be noted that no single component of the media of the invention makes it possible to obtain a stability greater than 25%.

A control of viability and of revival in culture was carried out on batches after being frozen for 7 months. Thus, 4 ampoules of cells frozen in a solution of Plasmion 67%/HSA 33% (see Example 1) were thawed after 7 months according to the protocol of Example 2. The four ampoules were cultured in a 75 $cm^2$ flask. The viability and revival in culture were determined and are presented in Table 11.

These results show a high percentage viability and a good revival of the cells in culture. The cells exhibit normal adherence and a normal refringent appearance. The passages P1 and P2 (175 $cm^2$) were carried out under normal culture conditions.

Example 4

Improvement of the Revival in Culture

In order to study the revival in culture of the cells treated according to the invention, tests were carried out on different media supplemented with cell stabilizing agents, and in particular with different concentrations of glycerol.

4.1. Preparations of the Media

A [lacuna] is prepared according to the procedure described above, and then glycerol is next added at the concentrations indicated in the table below, or, as a control, DMSO. Briefly, for a volume of 10 ml of a freezing medium at 67% plasmion, 33% HSA and 2.5% glycerol, the concentrations by volume of the components are:

HSA/Plasmion medium: 9.75 ml

Glycerol: 0.25 ml or 0.312 g of glycerol 10 ml of HSA/Plasmion→6.7 ml of Plasmion 9.75 ml of HSA/Plasmion medium→6.53 ml of plasmion 10 ml of HSA/Plasmion medium→3.3 ml of HSA 9.75 ml of HSA/Plasmion medium→3.21 ml of HSA

TABLE 12

Composition of the supplemented media

| MEDIA Q:10 ml | PLASMION (ml) | HSA (ml) | DMSO (ml) | GLYCEROL (ml) |
|---|---|---|---|---|
| HP + 5% DMSO | 6.3 | 3.13 | 0.5 | |
| HP + 2.5% DMSO | 6.53 | 3.21 | 0.25 | |
| HP + 1% DMSO | 6.63 | 3.26 | 0.1 | |
| HP + 10% GLYCEROL | 6.03 | 2.97 | | 1 (1.25 g) |
| HP + 5% GLYCEROL | 6.3 | 3.13 | | 0.5 (0.625 g) |
| HP + 2.5% GLYCEROL | 6.53 | 3.21 | | 0.25 (0.312 g) |
| HP + 1% GLYCEROL | 6.63 | 3.26 | | 0.1 (0.125 g) |

4.2. Study of Cell Viability

The freezing was carried out under the conditions described in Example 1. The results obtained after thawing on day 7 are presented in Table 13. They show that, in the presence of glycerol in a proportion of less than about 5%, the mean cell viability observed after thawing is greater than 70%. In particular, a mean viability of 84% is observed in the presence of 1% glycerol.

4.3. Study of the Revival in Culture

The revival in culture is a variable characterizing the state of poliferative cells after thawing. It is estimated, in this example, by the time necessary for the cells to reach confluence. To determine this parameter, after thawing, the cell concentration is adjusted to between $2.5 \times 10^5$ and $3.5 \times 10^5$ C/ml then the cells are maintained in culture. The results obtained are presented in Table 14. They show that the revival in culture occurs more rapidly when the cells have been frozen in a medium supplemented with glycerol (3.5 to 4 days) than in a medium without glycerol (4 to 5 days). These results also show that the cell stabilizing agent is advantageously introduced in an amount of 0.5 to 2.5%.

Example 5

Programmed Freezing Tests

Programmed freezing tests were carried out in order to determine if a better control of the freezing parameters could influence the quality of the biological material. In particular, a freezing procedure which makes it possible to avoid superfusion of the medium was tested. To do this, freezing tests assisted by a liquid nitrogen freezer Kryosave planar from Flobio were carried out, in comparison with freezing tests using alcohol (isopropanol) according to Example 1. The freezing is performed in a freezing medium at 67% plasmion, 33% HSA and 2.5% or 1% glycerol. The advantage of this system is to carry out a rapid freezing of the cells (or of the material), and a controlled decrease in the temperature of the cells and of the medium, which makes it possible to avoid the melting point of any frozen medium. For that, the melting point is determined beforehand by observing, during freezing using alcohol, its position in terms of temperature and over time. In this example, the temperature was reduced to −40° C. over 10 minutes from −8° C., because the melting point for the material used was at this level and the medium was rising towards 0° C. After freezing on day 7, the cell viability and the revival in culture after 24 hours are determined. The results obtained are presented in Tables 15 and 16.

These results clearly show a high cell viability, in all the freezing schemes and media of the invention tested. In addition, they show a good revival of the cells in culture, in particular for media comprising 1% glycerol. In this case, indeed, a yield greater than 70% is observed 24 hours after thawing. Moreover, in the case of a controlled programmed freezing (Kryosave), the cell layer observed after 24 hours is good and a very limited number of dead cells appears.

TABLE 3

Composition and preparation of the media

| Medium | 20% HSA Solution | Plasmion | g/l HSA | g/l Gelatin | H/G Weight ratio | Preparation (10 ml) |
|---|---|---|---|---|---|---|
| 10H/90P | 10% v | 90% v | 20 | 27 | 0.740 | 1 ml HSA 9 ml P |
| 20H/60P | 20% v | 80% v | 40 | 27 | 1.666 | 2 ml HSA 6 ml P |
| 30H/70P | 30% v | 70% v | 60 | 21 | 2.657 | 3 ml HSA 7 ml P |

TABLE 3-continued

Composition and preparation of the media

| Medium | 20% HSA Solution | Plasmion | g/l HSA | g/l Gelatin | H/G Weight ratio | Preparation (10 ml) |
|---|---|---|---|---|---|---|
| 40H/60P | 40% v | 60% v | 80 | 18 | 4.444 | 4 ml HSA 6 ml P |
| 50H/50P | 50% v | 50% v | 100 | 15 | 6.666 | 5 ml HSA 5 ml P |
| 60H/40P | 60% v | 40% v | 120 | 12 | 10 | 6 ml HSA 4 ml P |
| 70H/30P | 70% v | 30% v | 140 | 9 | 15.555 | 7 ml HSA 3 ml P |
| 60H/20P | 80% v | 20% v | 160 | 6 | 26.666 | 8 ml HSA 2 ml P |
| 90H/10P | 90% v | 10% v | 160 | 3 | 60 | 9 ml HSA 1 ml P |

TABLE 4

Experiment #1 - Thawing on day 5

| Freezing medium | % viability on thawing | Number of cells per ampoule (*$10^7$) | Culture |
|---|---|---|---|
| 67H/33P | 50.8 | 0.975 | Yes |
| 50H/50P | 63.2 | 0.51 | Yes |
| 33H/67P | 71.4 | 0.42 | Yes |
| H/P + Glycine 5% | 49.4 | 0.51 | Yes |
| H/P + Glycine 1% | 54.8 | 0.54 | Yes |

TABLE 5

Experiment #1 - Thawing on day 6

| Freezing medium | % viability on thawing | Number of cells per ampoule (*$10^7$) | Culture |
|---|---|---|---|
| 67H/33P | 76.2 | 0.69 | Yes |
| 50H/50P | 65.9 | 0.69 | Yes |
| 33H/67P | 55.1 | 0.76 | Yes |
| H/P + Glycine 5% | 63.2 | 0.21 | Yes |
| H/P + Glycine 1% | 55.6 | 0.25 | Yes |

TABLE 6

Experiment #2 - Thawing on day XX

| Freezing medium | % viability on thawing | Number of cells per ampoule (*$10^6$) | Culture |
|---|---|---|---|
| 67H/33P | 55.2 | 10.4 | Yes |
|  | 43.2 | 13.2 | Yes |
| 50H/50P | 60.9 | 28.8 | Yes |
|  | 63.7 | 26 | Yes |
|  | 70.5 | 12.1 | Yes |
|  | 71.7 | 9 | Yes |
| 33H/67P | 73.5 | 12.8 | Yes |
|  | 82 | 8.55 | Yes |

TABLE 7

Experiment #3 - Thawing on day 5

| Freezing medium | % viability on thawing | Number of cells per ampoule (*$10^7$) | Culture |
|---|---|---|---|
| 10H/90P | nd | nd | nd |
| 20H/80P | 53.4 | 1.10 | Yes |
| 30H/70P | 54.4 | 0.86 | Yes |
| 40H/60P | 53.5 | 1.29 | Yes |
| 50H/50P | 46.3 | 1.00 | Yes |
| 60H/40P | 48 | 1.13 | Yes |
| 70H/30P | nd | nd | nd |
| 80H/20P | 59.2 | 1.14 | Yes |
| 90H/20P | 61.7 | 0.90 | Yes |

TABLE 8

Experiment #3 - Thawing on day 13

| Freezing medium | % viability on thawing | Number of cells per ampoule (*$10^7$) | Culture |
|---|---|---|---|
| 10H/90P | 49.2 | 0.94 | Yes |
| 20H/80P | 54.5 | 1.12 | Yes |
| 30H/70P | nd | nd | nd |
| 40H/60P | 50.6 | 1.20 | Yes |
| 50H/50P | 58 | 0.73 | Yes |
| 60H/40P | 49.4 | 1.20 | Yes |
| 70H/30P | 54.8 | 0.90 | Yes |
| 80H/20P | 64.7 | 0.99 | Yes |
| 90H/20P | 50 | 0.79 | Yes |

TABLE 9

Experiment #4 - Thawing on day 8

| Freezing medium | % viability on thawing | Number of cells per ampoule (*$10^7$) | Culture |
|---|---|---|---|
| 50H/50P | 61.8 | 0.83 | Yes |
| 30H/70P | 68 | 0.75 | Yes |
| 70H/30P | 59.2 | 0.74 | Yes |
| 100P | 21.9 | 0.96 | No |

TABLE 10

Experiment #4 - Thawing on day 19

| Freezing medium | % viability on thawing | Number of cells per ampoule (*$10^7$) | Culture |
|---|---|---|---|
| 50H/50P | 77.3 | 0.66 | Yes |
| 30H/70P | 61.2 | 0.735 | Yes |
| 70H/30P | 62.7 | 0.85 | Yes |
| 100P | 6.5 | 0.69 | No |

TABLE 11

Viability and revival in culture after thawing at 7 months

| | Viability | Total no. of cells | Number of live cells | Adherent cells 24 h | Adherent cells 72 h P1 | Adherent cells 120 h P2 | Yield 24 h |
|---|---|---|---|---|---|---|---|
| Amp. 1 | 79.8% | 3.13 10⁷ | 2.5 10⁷ | 1.36 10⁷ | | | 54.4% |
| Amp. 2 | 74.5% | 3.1 10⁷ | 2.31 10⁷ | | 1.66 10⁷ | 3.48 10⁷ | |
| Amp. 3 | 79% | 2.72 10⁷ | 2.17 10⁷ | 1.35 10⁷ | | | 62.2% |
| Amp. 4 | 76.6% | 3.25 10⁷ | 2.49 10⁷ | NA | NA | NA | |

TABLE 13

Glycerol-supplemented media

| | V1 | V2 | V3 | Mean viability |
|---|---|---|---|---|
| HP + 10% Glycerol | 41% | 50% | 48.5% | 46.5% |
| HP + 5% Glycerol | 70% | 70% | 64% | 68% |
| HP + 2.5% Glycerol | 80.5% | 80% | 79% | 79.8% |
| HP + 1% Glycerol | 84% | 82% | 87% | 84% |
| HP | 78% | 75% | 73% | 75% |
| HP + 5% DMSO | 81% | 91% | 93% | 88% |
| HP + 2.5% DMSO | 94% | 89% | 92% | 91% |
| HP + 1% DMSO | 93% | 92% | 89% | 91% |

TABLE 14

Study of the revival in culture

| | Confluence 1 75 cm² | Confluence 2 75 cm² | Confluence 3 25 cm² |
|---|---|---|---|
| HP + 10% Glycerol | no sub-culturing | no sub-culturing | no sub-culturing |
| HP + 5% Glycerol | 4 | 4 | 3.5 |
| HP + 2.5% Glycerol | 4 | 4 | 3.5 |
| HP + 1% Glycerol | 4 | 4 | 3.5 |
| HP | 5 | 5 | 4 |

TABLE 15

Programmed freezing tests in HP + 1% Glycerol medium

| | Viability | Cell conc./ml | Total live cells | Adh. cells 24 h | Dead cells in susp. | Yield |
|---|---|---|---|---|---|---|
| Kryosave 1 | 88% | 7.3 × 10⁵ | 2.19 × 10⁷ | 1.74 × 10⁷ | 4.95 × 10⁶ | 79% |
| C isopropanol 1 | 77% | 6 × 10⁵ | 1.81 × 10⁷ | 1.34 × 10⁷ | 1.32 × 10⁷ | 74% |
| Kryosave 2 | 83% | 8.4 × 10⁵ | 2.53 × 10⁷ | 1.95 × 10⁷ | 3.3 × 10⁶ | 77% |
| C isopropanol 2 | 81.5% | 8 × 10⁵ | 2.41 × 10⁷ | 1.02 × 10⁷ | 1.12 × 10⁷ | 42% |

All the cells in each ampoule are placed in culture in 75 cm² flasks

TABLE 16

Programmed freezing tests in HP + 2.5% Glycerol medium

| | Viability | Cell conc./ml | Total live cells | Adh. cells 24 h | Dead cells in susp. | Yield |
|---|---|---|---|---|---|---|
| Kryosave 1 | 85% | 1.54 × 10⁶ | 4.62 × 10⁷ | 2.07 × 10⁷ | 5.1 × 10⁶ | 45% |
| Isopropanol 1 | 82% | 1.12 × 10⁶ | 3.36 × 10⁷ | 1.03 × 10⁷ | 6.9 × 10⁶ | 30% |
| Kryosave 2 | 78% | 1.76 × 10⁶ | 5.28 × 10⁷ | 2.9 × 10⁷ | 3.9 × 10⁶ | 55% |
| Isopropanol 2 | 69% | 9.7 × 10⁵ | 2.91 × 10⁷ | 1.45 × 10⁷ | 5.25 × 10⁶ | 50% |

What is claimed is:

1. A medium for preservation of frozen biological material, wherein the medium is directly injectible into an organism and consists of an isotonic saline solution, modified fluid gelatin and human serum albumin, and wherein the medium lacks a toxic agent.

2. The medium according to claim 1, wherein the isotonic saline solution is isotonic with plasma.

3. The medium according to claim 2, wherein the isotonic saline solution consists of sodium chloride, potassium chloride, magnesium chloride, and sodium lactate.

4. The medium according to claim 3, wherein the isotonic saline solution consists of 2 to 5 g/l of sodium chloride, 0.05 to 0.5 g/l of potassium chloride, 0.05 to 0.2 g/l of magnesium chloride and 0.5 to 4 g/l of sodium lactate.

5. The medium according to claim 2, wherein the isotonic saline solution consists of sodium chloride, potassium chloride, calcium chloride and sodium lactate.

6. The medium according to claim 5, wherein the isotonic saline solution is Ringer's lactate.

7. The medium according to claim 1, wherein the modified fluid gelatin is a chemically modified collagen hydrolysis product.

8. The medium according to claim 7, wherein the chemically modified collagen hydrolysis product has an average molecular weight of between 10 kD and 100 kD.

9. The medium according to claim 8, wherein the chemically modified and pharmaceutically acceptable collagen hydrolysis product has an average molecular weight of between 15 kD and 40 kD.

10. The medium according to claim 7, wherein the modified fluid gelatin is chemically modified by reacting collagen with succinic, citraconic, itaconic, aconitic, or maleic anhydride.

11. The medium according to once claim 1, wherein the human serum albumin is of plasma origin.

12. The medium according to claim 1, wherein the medium has a human serum albumin (grams/liter)/gelatin (grams/liter) ratio of between 0.5 and 100.

13. The medium according to claim 12, wherein the human serum albumin/gelatin ratio is between 0.74 and 60.

14. The medium according to claim 12, wherein the human serum albumin/gelatin ratio is equal to 0.74, 1.66, 3.3, 6.66, 13.4, 26.66, or 60.

15. A composition comprising a population of genetically modified cells and the medium according to claim 1.

16. The composition of claim 15, wherein the cells are blood cells.

17. The composition according to claim 16 wherein the blood cells are platelets.

18. A composition comprising a population of bone marrow cells and the medium according to claim 1.

19. A composition comprising viral particles and the medium according to claim 1.

20. The composition according to claim 19, wherein the viral particles are replication defective recombinant viral particles.

21. A composition comprising a population of viral particle-producing cells and the medium according to claim 1.

22. A process for storing isolated cells or viral particles comprising suspending the isolated cells or viral particles in a medium according to claim 1, and freezing the suspension.

23. The process according to claim 22, wherein the biological material is isolated cells and wherein a percentage of cell viability after thawing is greater than or equal to 50%.

24. The process according to claim 23, wherein the percentage of cell viability after thawing is greater than or equal to 60%.

25. The process according to claim 24, wherein the percentage of cell viability after freezing and thawing is greater than or equal to 70%.

26. A medium for preservation of frozen biological material, wherein the medium is directly injectible into an organism and consists of an isotonic saline solution, modified fluid gelatin, human serum albumin and between 0.5% and 5% by weight of a biocompatible cell stabilizing agent, and wherein the medium lacks a toxic agent.

27. The medium according to claim 26, wherein the cell stabilizing agent is selected from the group consisting of glycine, glycerol, sucrose, and glucose.

28. A frozen biological composition comprising an isotonic saline solution, modified fluid gelatin, human serum albumin and at least one of animal cells or viral particles; wherein the percentage of viability of the cells or viral particles is greater than or equal to 50% upon thawing of the frozen biological composition, and the frozen biological composition lacks any agent which would be toxic to an organism injected with the thawed biological composition.

29. The frozen biological composition according to claim 28, wherein the isotonic saline solution is isotonic with plasma.

30. The frozen biological composition according to claim 29, wherein the isotonic saline solution comprises sodium chloride, potassium chloride, magnesium chloride and sodium lactate.

31. The frozen biological composition according to claim 30, wherein the isotonic saline solution comprises 2 to 5 g/l of sodium chloride, 0.05 to 0.5 g/l of potassium chloride, 0.05 to 0.2 g/l of magnesium chloride and 0.5 to 4 g/l of sodium lactate.

32. The frozen biological composition according to claim 29, wherein the isotonic saline solution comprises sodium chloride, potassium chloride, calcium chloride and sodium lactate.

33. The frozen biological composition according to claim 32, wherein the isotonic saline solution is Ringer's lactate.

34. The frozen biological composition according to claim 28, wherein the modified fluid gelatin is a chemically modified collagen hydrolysis product.

35. The frozen biological composition according to claim 34, wherein the chemically modified collagen hydrolysis product has an average molecular weight of between 10 kD and 100 kD.

36. The frozen biological composition according to claim 34, wherein the modified fluid gelatin is chemically modified by reacting collagen with succinic, citraconic, itaconic, aconitic or maleic anhydride.

37. The frozen biological composition according to claim 28, wherein the human serum albumin is of plasma origin.

38. The frozen biological composition according to claim 28, having a human serum albumin to modified fluid gelatin ratio of between 0.5 and 100, wherein both the human serum albumin and modified fluid gelatin are measured in grams per liter.

39. The frozen biological composition according to claim 38, wherein the human serum albumin to modified fluid gelatin ratio is between 0.74 and 60.

40. The frozen biological composition according to claim 38, wherein the human serum albumin to modified fluid gelatin ratio is selected from the group consisting of 0.74, 1.66, 3.3, 6.66, 13.4, 26.66 and 60.

41. The frozen biological composition according to claim 28, further comprising between 0.5% and 5% by weight of a biocompatible cell stabilizing agent.

42. The frozen biological composition according to claim 41, wherein the biocompatible cell stabilizing agent is selected from the group consisting of glycine, glycerol, sucrose and glucose.

43. The frozen biological composition according to claim 28, containing genetically modified cells.

44. The frozen biological composition according to claim 28, containing blood cells.

45. The frozen biological composition according to claim 44, wherein the blood cells are platelets.

46. The frozen biological composition according to claim 28, containing bone marrow cells.

47. The frozen biological composition according to claim 28, containing replication defective recombinant viral particles.

* * * * *